US00PP33998P2

(12) United States Plant Patent
Thiede

(10) Patent No.: US PP33,998 P2
(45) Date of Patent: Mar. 8, 2022

(54) ***DIANTHUS* PLANT NAMED 'KLEDG20336'**

(50) Latin Name: ***Dianthus caryophyllus* x *gratianopolitanus***
Varietal Denomination: KLEDG20336

(71) Applicant: Klemm+Sohn GmbH & Co. KG, Stuttgart (DE)

(72) Inventor: Lena Thiede, Bempflingen (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/379,609

(22) Filed: Jul. 19, 2021

(51) Int. Cl.
*A01H 5/02* (2018.01)
*A01H 6/30* (2018.01)

(52) U.S. Cl.
USPC ..... Plt./273
CPC ..... *A01H 6/30* (2018.05)

(58) Field of Classification Search
USPC ..... Plt./273
CPC ..... A01H 5/0255
See application file for complete search history.

(56) References Cited

PUBLICATIONS

PLUTO UPOVROM Plant Variety Database 20210923 Citation for 'Kledg20336' as per QZ PBR 20211322; Jun. 11, 2021; 1 page.*

* cited by examiner

*Primary Examiner* — Kent L Bell
(74) *Attorney, Agent, or Firm* — Weatherly IP Solutions, LLC; James M. Weatherly

(57) ABSTRACT

A new *Dianthus* plant named 'KLEDG20336' particularly distinguished by dark a purple flower color with violet spots and single filling.

1 Drawing Sheet

Genus and species: *Dianthus caryophyllus* x *gratianopolitanus*.
Variety denomination: 'KLEDG20336'.

BACKGROUND OF VARIETY 'KLEDG20336'

The present invention comprises a new and distinct variety of *Dianthus*, botanically known as *Dianthus* sp. and hereinafter referred to by the variety name 'KLEDG20336'. 'KLEDG20336' is a selection that resulted from a cross pollination of the proprietary female *Dianthus* line 'DSS-2014-1022' (unpatented) and the proprietary male *Dianthus* line 'DSS-2013-0033'.

In June of 2015, the proprietary female *Dianthus* line 'DSS-2014-1022' and the proprietary male *Dianthus* line 'DSS-2013-0033' were cross pollinated in Stuttgart, Germany and seeds were obtained. The seeds were sown and plants were grown for evaluation. A plant line was selected in July of 2016 in Stuttgart, Germany, and named 'KLEDG20336'. In July of 2016, 'KLEDG20336' was first vegetatively propagated by vegetative cuttings. 'KLEDG20336' was found to reproduce true to type in successive generations of asexual propagation via vegetative cuttings in Stuttgart, Germany.

SUMMARY OF VARIETY 'KLEDG20336'

The following are the most outstanding and distinguishing characteristics of this new variety when grown under normal horticultural practices in Stuttgart, Germany.

1. Dark purple flower color with violet spots; and
2. Single filling.

DESCRIPTION OF THE PHOTOGRAPH

This new *Dianthus* plant is illustrated by the accompanying photograph which shows the overall plant habit of the variety 'KLEDG20336' grown in a pot. The photograph is of a 14-week-old plant in Stuttgart, Germany under greenhouse conditions in March 2019.

DESCRIPTION OF THE NEW VARIETY 'KLEDG20336'

The following detailed descriptions set forth the distinctive characteristics of 'KLEDG20336'. Data was collected on seven-month-old plants potted and cultivated in Stuttgart, Germany in April of 2021. Color references are to The R.H.S. Colour Chart of The Royal Horticultural Society of London (R.H.S.), 5$^{th}$ edition.

Classification:
- *Family*.—Caryophyllaceae.
- *Species*.—*Dianthus caryophyllus* x *gratianopolitanus*.
- *Common name*.—Pot carnation.

Parentage:
- *Female parent*.—The *Dianthus* 'DSS-2014-1022'(unpatented).
- *Male parent*.—The *Dianthus* 'DSS-2013-0033'(unpatented).

Propagation:
- *Propagation type*.—Vegetative stem cuttings.
- *Time to produce a rooted young plant*.—14 to 18 days.
- *Root description*.—Young roots: RHS 161D. Mature roots: RHS 199C
- *Rooting habit*.—Lanceolate..

Plant description:
- *Form*.—Upright.
- *Height*.—19.0 cm to 22.0 cm.
- *Diameter or spread*.—30.0 cm to 35.0 cm.

Lateral branches:

*Length.*—8.0 cm to 12.0 cm.

*Diameter.*—4.0 cm to 7.0 cm.

*Internode length.*—2.0 cm to 4.0 cm.

*Number of internodes per branch/stem.*—6 to 9.

*Node length.*—0.2 cm to 0.4 cm.

*Node diameter.*—0.1 cm to 0.2 cm.

*Texture.*—Smooth.

*Color.*—RHS 189A.

*Branch/stem.*—Lower part solid, upper part hollow.

Foliage description:

*Arrangement.*—Opposite.

*Length.*—2.0 cm to 5.0 cm.

*Width.*—0.3 cm to 0.5 cm.

*Shape.*—Ovate.

*Apex.*—Acute.

*Base.*—Obtuse.

*Margin.*—Entire.

*Texture.*—Upper and lower surfaces: Smooth.

*Immature leaf color.*—Upper surface: RHS 189A. Lower surface: RHS 189A.

*Mature leaf color.*—Upper surface: RHS 137B. Lower surface: RHS 137C

*Venation pattern.*—No venation.

Flower description:

*Flower type and habit.*—Single flower, round/wavy shape.

*Fragrance.*—Present.

*Natural flowering season.*—Spring to Autumn.

*Position of flowers relative to the foliage.*—Above foliage.

*Number of flowers per spray.*—5 to 8.

*Flower longevity on the plant.*—14 to 21 days.

*Flower buds.*—Length: 1.3 cm to 1.8 cm. Diameter: 0.5 cm to 0.6 cm. Shape: Elliptic. Color: RHS 147A. Extrusion of the styles at the bud stage: Absent.

*Corolla.*—Quantity of petals and arrangement: 5. Corolla height: 0.6 cm to 1.0 cm. Petal length: 2.7 cm to 3.0 cm. Petal width: 1.6 cm to 2.0 cm. Petal shape: Spoon shaped. Petal apex: Obtuse. Petal base: Acute. Petal margin: Sparsely serrated. Depth of petal margin: Low. Petal texture: Upper and lower surfaces: Smooth. Petal color: Immature: Upper surface: RHS 77A and RHS 77C. Lower surface: Middle RHS 76 B, border RHS 76A. Mature: Upper surface: RHS 77A and RHS 76A. Lower surface: RHS 76B. Calyx: Quantity of sepals: Composed of 5 sepals. Shape: Cylindric. Calyx height: 1.8 cm to 2.2 cm. Calyx diameter (at the apex): 0.4 cm to 0.6 cm. Sepal texture: Upper and lower surfaces: Smooth. Sepal color: Upper surface: RHS 137A. Lower surface: RHS 137D.

Peduncles:

*Length.*—1.0 to 2.0 cm (last internode), whole stem 10.0 cm.

*Diameter.*—0.1 cm to 0.2 cm.

*Strength.*—Moderate.

*Texture.*—Smooth.

*Color.*—RHS 189A.

Reproductive organs:

*Stamens.*—Quantity per flower: 8 to 12. Filament length: 1.5 cm to 2.0 cm. Filament color: RHS 155B. Anther length: 0.15 cm. Anther diameter: 0.05 cm to 0.1 cm. Anther color: RHS 161A. Pollen amount: Moderate. Pollen color: Yellow-brownish.

*Pistils.*—Quantity per flower: 2 styles. Pistil length: 1.5 cm to 2.0 cm. Style length: 1.0 cm to 1.5 cm. Style color: RHS 69D. Stigma shape: Filamentous. Stigma color: RHS 77B. Ovary size: 0.6 cm to 0.8 cm. Ovary shape: Oval. Ovary color: RHS 145C, top is RHS 145A.

Fruit and seed set: Seed sometimes observed but information not available.

Disease and insect/pest resistance: No special observations were made.

COMPARISON OF 'KLEDG20336' WITH PARENTAL LINES AND KNOWN VARIETY

When 'KLEDG20336' is compared to the female parental line 'DSS-2014-1022' and the male parental line 'DSS-2013-0033', the following differences are noted in Table 1:

TABLE 1

Comparison with Parental Lines

| Trait or characteristic | 'KLEDG20336' | Female parent | Male Parent |
|---|---|---|---|
| Flower color | Dark purple, violet spots | Dark purple red | Violet, dark purple center |
| Filling | Single | Double | Single |

When 'KLEDG20336' is compared to the commercial line 'KLEDG13146' (U.S. Plant Pat. No. 25,877), the following differences are noted in Table 2:

TABLE 2

Comparison with Similar Variety

| Trait or characteristic | 'KLEDG20336' | Commercial line: 'KLEDG13146' |
|---|---|---|
| Flower color | Dark purple, violet spots | Purple, lavender speckles |
| Flower pattern | Two violet spots | Many small speckles |

I claim:

1. A new and distinct variety of *Dianthus* plant named 'KLEDG20336' as shown and described herein.

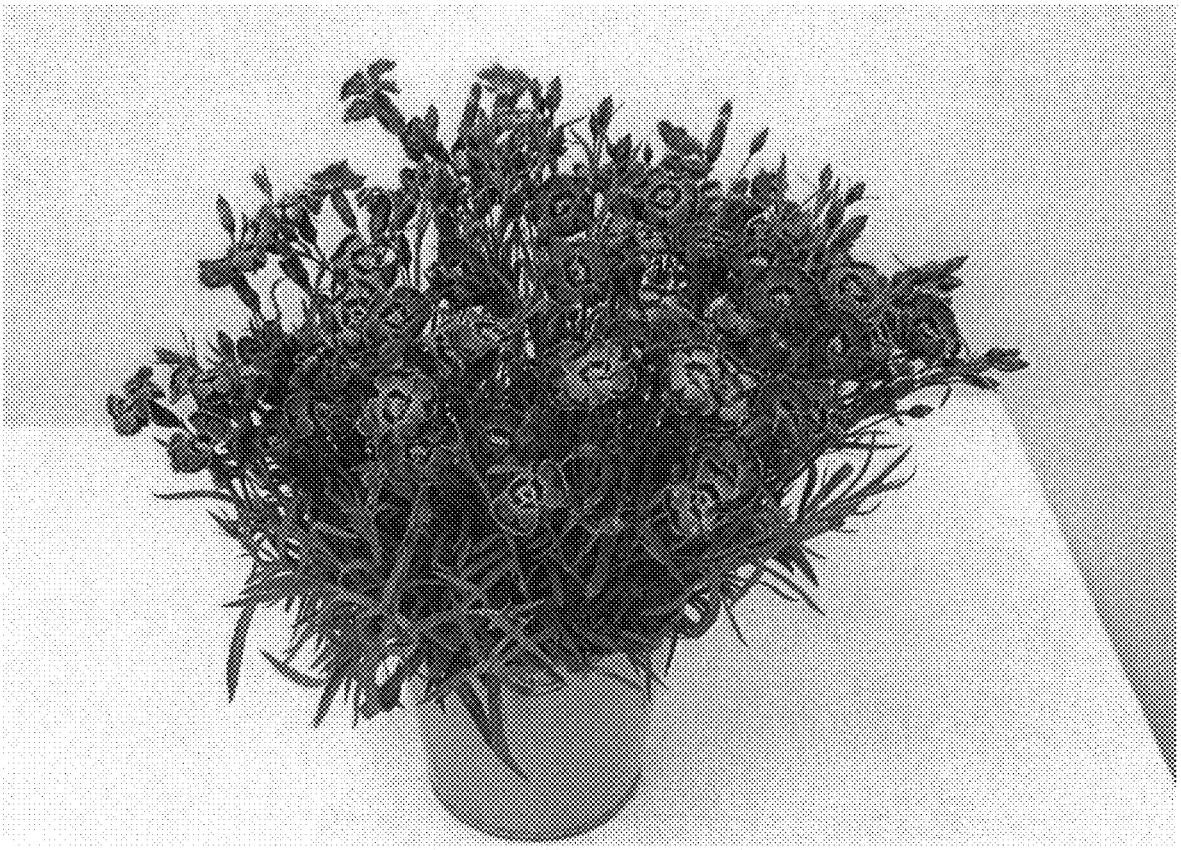

* * * * *